United States Patent [19]

Schwabe et al.

[11] Patent Number: 4,891,400

[45] Date of Patent: * Jan. 2, 1990

[54] SILICONE MOLDING COMPOUNDS

[75] Inventors: Peter Schwabe; Reiner Voigt; Ottfried Schlak, all of Leverkusen, Fed. Rep. of Germany

[73] Assignee: Bayer Aktiengesellschaft, Leverkusen, Fed. Rep. of Germany

[*] Notice: The portion of the term of this patent subsequent to Apr. 12, 2005 has been disclaimed.

[21] Appl. No.: 204,952

[22] Filed: Jun. 6, 1988

Related U.S. Application Data

[63] Continuation of Ser. No. 903,010, Sep. 2, 1986, abandoned.

[30] Foreign Application Priority Data

Sep. 13, 1985 [DE] Fed. Rep. of Germany ....... 3532687

[51] Int. Cl.$^4$ .............................................. C08K 5/01
[52] U.S. Cl. .................................... 524/745; 524/425; 524/451; 524/474; 524/487; 524/488; 524/490; 524/423; 524/788; 524/789; 524/860; 524/861; 524/862; 524/848
[58] Field of Search ............... 524/425, 451, 474, 487, 524/488, 490, 423, 788, 789, 745, 860, 861, 862, 848

[56] References Cited

U.S. PATENT DOCUMENTS

| | | | |
|---|---|---|---|
| 3,565,825 | 2/1971 | Antelman | 252/431 |
| 4,035,453 | 7/1977 | Hittmair et al. | 528/31 |
| 4,100,124 | 7/1978 | Ichikawa et al. | 524/730 |
| 4,357,438 | 11/1982 | Sattlegger et al. | 528/12 |
| 4,614,758 | 9/1986 | Schwabe et al. | 524/487 |
| 4,737,537 | 4/1988 | Schwabe et al. | 524/481 |

FOREIGN PATENT DOCUMENTS

| | | |
|---|---|---|
| 0043501 | 1/1982 | European Pat. Off. |
| 0152887 | 8/1985 | European Pat. Off. |
| 0158141 | 10/1985 | European Pat. Off. |
| 0166107 | 1/1986 | European Pat. Off. |

OTHER PUBLICATIONS

R. C. Craig, *Restorative Dental Materials*, The C. V. Moosbe Comp., St. Louis, 1980, pp. 195–196.

*Primary Examiner*—Melvyn I. Marquis
*Attorney, Agent, or Firm*—Sprung Horn Kramer & Woods

[57] ABSTRACT

An addition or condensation cross-linking molding or lining compound based on silicones comprising
(a) an organo polysiloxane containing reactive end groups,
(b) a catalyst,
(c) a filler, and
(d) an isoparaffin having 8 to 24 carbon atoms.
The compounds being particularly useful as dental molding compositions.

15 Claims, No Drawings

SILICONE MOLDING COMPOUNDS

This application is a continuation of application Ser. No. 903,010, filed Sep. 2, 1986, now abandoned.

BACKGROUND OF THE INVENTION

1. Field of the Invention

The present invention relates to masses based on polysiloxanes and containing isoparaffin for use as molding and/or lining compounds, in particular in dentistry. These compounds are silicone pastes cross-linked by condensation or addition reactions for producing exact impressions of dentate, partially dentate or nondentate jaws and plaster casts in dentistry.

2. Background Information

Silicone pastes are widely used as molding compounds in dentistry. They generally consist of a silicone oil based on a polydimethyl siloxane containing hydroxyl end groups and mixed with fillers and a liquid or pasty curing component containing a metal salt of a monocarboxylic acid as a catalyst and a silicic acid ester as a cross-linking agent. The mixture of silicone oil and fillers may be varied in consistency according to the method of application to be employed. (See, e.g., W. Noll, *Chemie und Technologie der Silicone,* Verlag Chemie, Weinheim, 2nd Edition, 1964, pages 339-340).

The two components are mixed together before use and cross-link within 2-5 minutes at room temperature due to a polycondensation reaction. This reaction gives rise to small quantities of alcohol in addition to the cross-linked silicone rubber, and the alcohol formed slowly diffuses out of the rubber to produce linear shrinkage which causes inaccuracies in the molding.

The linear shrinkage is much less in the vinyl silicone molding compounds which have only been known in the last few years. These masses consist of two pastes, a basic paste containing silicone oil, filler and cross-linking agent and a catalyst paste containing silicone oil, filler and catalyst.

The silicone oil used in these vinyl silicone compositions is a polydimethyl siloxane containing vinyl end groups, the cross-linking agent contains the reactive SiH groups and the catalyst preferably consists of a platinum complex. In addition to the greater dimensional accuracy of the molding obtained with this system is the advantage that the basic paste and catalyst paste can be more accurately dosed since the pastes have the same viscosity and are mixed in proportions of 1:1. In addition, the pastes are completely flavourless and odourless (see e.g. R.C. Craig, *Restorative Dental Materials,* The C.V. Moosbe Comp., St. Louis, 1980 page 195 et seq).

SUMMARY OF THE INVENTION

In the course of further attempts to improve and modify such molding compounds, it has surprisingly been found that isoparaffins, in particular those having 8 to 24 carbon atoms, can be mixed with such substances to produce high quality molding compounds.

The present invention thus relates to molding and lining compounds, in particular for dentistry, which are based on silicones and cross-linked by addition or condensation reactions and consist of (a) organopolysiloxanes having reactive end groups,
(b) optionally organopolysiloxanes without reactive end groups,
(c) optionally organopolysiloxanes acting as cross linking agents,
(d) catalysts,
(e) fillers and optionally other conventional additives and/or auxiliary agents, characterised in that in addition they contain
(f) isoparaffins having 8 to 24 carbon atoms.

The present invention thus relates to the use of isoparaffins for pasty silicone masses in which the isoparaffins are used in a quantity of 1-50% by weight, preferably 5-30% by weight and preferably consist of isohexadecane and isoeicosane.

The invention further relates to silicone pastes, in particular silicone molding and lining compounds, containing such isoparaffins.

DETAILED DESCRIPTION OF THE INVENTION

The isoparaffins are preferably used in polysiloxane-based molding compounds which can be cured at room temperature. These may be subdivided, as already mentioned above, into systems which are cross-linked by addition reactions and those which are cross-linked by condensation reactions. The pastes according to the invention which are cross-linked by addition contain the following as essential components:

(a) organopolysiloxanes having two or more vinyl groups in the molecule,
(b) inorganic fillers (untreated or surface modified),
(c) organohydrogen polysiloxanes as cross-linking agents,
(d) a catalyst for accelerating the addition reaction,
(e) isoparaffin and
(f) conventional additives (e.g., to add flavor or fragrance).

The pastes according to the invention which are cross-linked by condensation with a liquid or pasty curing component consisting of a metal salt of a monocarboxylic acid ester as catalyst and a silicic acid ester as cross-linking agent contain the following as their main constituents:

(g) organopolysiloxanes having two or more hydroxyl groups per molecule,
(h) fillers,
(i) isoparaffins, and
(j) optionally conventional additives (e.g., substances to add fragrance and flavor).

The silicone masses according to the invention are distinguished by their stability in storage and good sliding qualities when the basic paste is mixed with the catalyst plate or the paste is mixed with curing component. They are suitable for making accurate impressions, especially for teeth, as they are reproduced accurately and in great detail in the plaster cast when the carefully mixed pastes are introduced into the oral cavity and left to solidify therein and the impression is then filled with a suspension of plaster and left to harden to form the model. This excellent result is obtained by virtue of the fact that the isoparaffin used according to the invention improves the wetting properties both of the mixed silicone molding composition on the moist surfaces of teeth and mucous membranes and of the crosslinked impression against the plaster suspension. Furthermore, when the silicone oil is partly replaced by the isoparaffin according to the invention in the system which is cross-linked by condensation, the shrinkage which occurs in the process of polymerization is reduced. Lining compositions which are cross-linked by addition reactions are distinguished by the low viscosity of the isoparaffin used according to the invention as diluent and the sharp and accurate reproduction of form, as well as the improved wetting properties of the mass in contact with the plaster cast which is to serve as model and the flexibility of the cross-linked lining mold. The latter can again be accurately filled with a plaster suspension due to the improved wetting properties.

The substances used in the above mentioned pastes which can be cured at room temperature are known in themselves.

The silicone oil (a) is a vinyl end-stopped polydimethyl siloxane having a viscosity preferably in the range of 500 to 5,000,000 mPas.s at 20° C.

Substances suitable as fillers (b) include, for example, powdered quartz and crystabilite, calcium sulphate, diatomaceous earth, talcum, calcium carbonate, and precipitated and pyrogenically prepared silicone dioxide with an untreated or modified surface.

The cross-linking agent (c) is a polydimethyl siloxane containing hydrogen atoms on at least two silicon atoms in the molecule.

Catalyst (d) may be, for example, a platinum complex prepared from hexachloroplatinic-(IV)-acid. These compounds are also known.

The isoparaffins to be used according to the invention contain 8 to 24 carbon atoms in the molecule, isohexadecane $C_{16}H_{34}$ and isoeicosane $C_{20}H_{42}$ being preferred.

The silicone oil (g) is a hydroxyl end stopped polydimethyl siloxane having a viscosity preferably in the range of 500 to 200,000 mPa.s at 20° C.

The fillers (h), isoparaffin (i) and additive (j) are the same substances as those described under (b), (e) and (f).

As already mentioned above, the vinyl silicone molding compounds which are cross-linked by addition reactions are supplied as 2-paste systems in various consistencies, namely a basic paste containing a silicone polymer, cross-linking agent and filler and a catalyst paste composed of a silicone polymer, filler and catalyst.

The two pastes, preferably brought together in proportions of 1:1 by weight and/or volume, are homogeneously mixed on a mixing block using a spatula, placed on a molding spoon and pressed against the part of the jaw of which an impression is required. After 2-5 minutes, the impression which has meanwhile cross-linked to form a rubber, may be removed from the mouth. The negative impression of the part of the jaw thus obtained is distinguished by the accurate reproduction of the markings on the jaw due to the fact that the mass containing the isoparaffin according to the invention has better wetting properties in contact with the constantly moist surfaces of the teeth and mucous membranes than vinyl silicone molding compounds not containing an isoparaffin. The improved wetting properties also demonstrate advantages when the impression is subsequently filled with a plaster slurry. Apart from these advantageous properties, an isoparaffin used as a liquid component reduces the cost of the paste formulations.

The condensation-cross-linking silicone molding compounds composed of silicone polymer and fillers and supplied in various consistencies are mixed in a specified proportion with a pasty or liquid component consisting of a metal salt, an organic acid as catalyst and a silicic acid ester as cross-linking agent and are then used as described above.

The condensation cross-linking silicone molding compounds containing isoparaffin in accordance with the invention were found not only to have advantages such as improved wetting and reduction in cost, but also undergo less shrinkage in the course of polymerization, since a proportion of the silicone oil has been replaced by isoparaffin and filler while the viscosity of the paste is the same as that of the known silicone molding compositions.

The compounds used for making copies of plaster casts are low viscosity, addition cross-linking lining compounds consisting of a basic paste containing a vinyl silicone oil, a cross-linking agent and filler and a catalyst paste containing a vinyl silicone oil, a filler and a catalyst. The two pastes are mixed together in a beaker in proportions by weight and/or volume in the range of from 1:1 to preferably 9:1, and the mixture is poured into a vessel containing the plaster model which is to be copied. The mass is found to be cross-linked after 10 to 25 minutes and when separated from the plaster cast it constitutes the mold for producing further plaster models. When isoparaffins were used according to the invention, it was found that in addition to the advantages mentioned above, such as improved wetting and reduction in cost, the cross-linked copying compositions contained far fewer air bubbles normally produced in the course of mixing and casting and were much more flexible than the copying molds previously obtained.

Finally, the improvement in wetting properties achieved by the isoparaffin used according to the invention was also found when the silicone oils were mixed with fillers to prepare the pastes.

The following examples, in which all parts are parts by weight, illustrate the invention.

EXAMPLE 1 (COMPARISON)

The basic paste of a medium viscosity, addition cross-linking dental impression molding compound was prepared by mixing in a kneader 340 parts of vinyl-end stopped polydimethyl siloxane having a viscosity of 10,000 mPa.s at 20° C., 210 parts of dimethyl hydrogen siloxy-end stopped polydimethyl siloxane having a viscosity of 120 mPa.s at 20° C., 380 parts of finest quartz powder, 50 parts of a pyrogenically produced silica having a specific surface area of 50 m²/g according to BET and 20 parts of an inorganic dye.

The catalyst paste was prepared by mixing in a kneader 548 parts of vinyl-end stopped polydimethyl siloxane having a viscosity of 5,000 mPa.s at 20° C., 400 parts of finest quartz powder, 50 parts of the above mentioned silica, 1.8 parts of titanium dioxide and 0.2 parts of a complex of platinum and divinyl-tetramethyl-disiloxane.

The basic paste and catalyst paste are mixed together in proportions by weight of 1:1 before they are used. The masses conform to specification DIN 13 913 and specification 19 of the American Dental Association. Drops of water on the cured rubber had a wetting angle of 122°.

EXAMPLE 2 (ACCORDING TO THE INVENTION)

A basic paste was prepared in a kneader by mixing 220 parts of vinyl-end stopped polydimethyl siloxane having a viscosity of 10,000 mPa.s at 20° C., 140 parts of dimethyl hydrogen siloxy-end stopped polydimethyl siloxane from Example 1, 150 parts of isoeicosane, 410 parts of finest quartz powder, 60 parts of the silica from Example 1 and 20 parts of an inorganic dye.

The catalyst paste was prepared in a kneader by mixing 368 parts of vinyl-end stopped polydimethyl siloxane having a viscosity of 5,000 mPa.s at 20° C., 150 parts of isoeicosane, 420 parts of finest quartz powder, 60 parts of the silica from Example 1, 1.8 parts of titanium dioxide and 0.2 parts of the platinum complex from Example 1.

The basic paste and catalyst paste were mixed in proportions by weight of 1:1 before they were used. The compositions conformed to the specifications mentioned in Example 1. The wetting angle of water drops on the cured rubber was 96°.

EXAMPLE 3 (COMPARISON)

A low viscosity condensation cross-linking dental impression molding compound was prepared in a kneader by mixing 650 parts of a hydroxyl-end stopped polydimethyl siloxane having a viscosity of 10,000 mPa.s at 20° C., 30 parts of water, 20 parts of the silica from Example 1. 280 parts of finest quartz powder and 20 parts of an inorganic dye.

The composition was mixed with a curing component of dibutyl tin dilaurate and polyethoxy siloxane in proportions by weight of 100:12 before use. The substance conformed to the specifications mentioned in Example 1. The wetting angle of water drops on the cured rubber was 113°.

EXAMPLE 4 (ACCORDING TO THE INVENTION)

The molding compound was prepared in a kneader by mixing 460 parts of hydroxyl-end stopped polydimethyl siloxane having a viscosity of 18,000 mPa.s at 20° C., 20 parts of water, 20 parts of the silica from Example 1, 200 parts of isoeicosane, 280 parts of finest quartz powder and 20 parts of an inorganic dye.

This composition and the curing component of dibutyl tin dilaurate and polyethoxy siloxane were mixed in proportions by weight of 100:8 before use. The composition conformed to the specifications indicated in Example 1. The wetting angle of water drops on the cross-linked rubber was 82°.

EXAMPLE 5 (COMPARISON)

The basic paste of an addition cross-linking lining compound was prepared in a kneader by mixing 550 parts of vinyl-end stopped polydimethyl siloxane having a viscosity of 10,000 mPa.s at 20° C., 200 parts of trimethyl-siloxy-end stopped polydimethyl siloxane having a viscosity of 120 mPa.s at 20° C., 200 parts of polydimethyl siloxane containing SiH groups and having a viscosity of 95 mPa.s at 20° C. and 50 parts of a precipitated and surface treated silica having a specific surface area of 90 m$^2$/g according to BET.

The catalyst paste was prepared in a kneader by mixing 540 parts of vinyl-end stopped polydimethyl siloxane having a viscosity of 10,000 mPa.s at 20° C., 400 parts of trimethyl siloxy-end stopped polydimethyl siloxane having a viscosity of 120 mPa.s at 20° C., 50 parts of the silica described above, 9.8 parts of an inorganic dye and 0.2 parts of the platinum-siloxane complex from Example 1.

The basic paste was mixed with the catalyst paste in proportions by weight of 9:1 before use. The cured lining mold contained air bubbles introduced in the process of mixing and casting. The wetting angle of the water drops on the cross-linked rubber was 125°.

EXAMPLE 6 (ACCORDING TO THE INVENTION)

The basic paste was prepared in a kneader by mixing 500 parts of the vinyl-end stopped dimethyl siloxane from Example 5, 250 parts of isoeicosane, 180 parts of the polydimethyl siloxane containing SiH groups from Example 5 and 70 parts of the silica from Example 5.

The catalyst paste was prepared in a kneader by mixing 480 parts of the vinyl-end stopped polydimethyl siloxane from Example 5, 450 parts of isoeicosane, 60 parts of the silica from Example 5, 9.8 parts of an inorganic dye and 0.2 parts of the platinum-siloxane complex from Example 1.

The basic paste and catalyst paste were mixed in proportions by weight of 9:1 before being used. The cross-linked lining mold contained only very few air bubbles introduced in the course of mixing and casting. Water drops on the cross-linked rubber had a wetting angle of 85°.

What is claimed is:

1. An addition cross-linking molding or lining compound based on silicones consisting essentially of
   (a) an organo polysiloxane containing two or more vinyl reactive end groups,
   (b) a catalyst comprising a platinum complex prepared from hexachloroplatinic - (IV) acid,
   (c) a filler,
   (d) an isoparaffin having 8 to 24 carbon atoms and
   (e) a cross-linking agent comprising a organohydrogen polysiloxane.

2. A compound according to claim 1, wherein said isoparaffin is selected from the group consisting of isohexadecane, isoeicosane and mixtures thereof.

3. A compound according to claim 1, wherein the isoparaffin is contained in an amount of 1 to 50% by weight.

4. A compound according to claim 1, wherein the isoparaffin is contained in an amount of 5 to 30% by weight.

5. A compound according to claim 1, wherein the organopolysiloxane is a silicone oil which is a vinyl-end-stopped polydimethyl siloxane having a viscosity of 500 to 5,000,000 mPa.s at 20° C.

6. A compound according to claim 1, wherein the filler is selected from the group consisting of powdered quartz, crystobalite, calcium sulphate, diatomaceous earth, talcum, calcium carbonate and precipitated and pyrogenically prepared silicone dioxide.

7. A compound according to claim 1, wherein a two-paste system is utilized, said two-paste system comprising a first paste which comprises a first portion of the organopolysiloxane, a first portion of said isoparaffin, said cross-linking agent and a first portion of the filler and a second paste which comprises a second portion of the organipolysiloxane, a second portion of said isoparaffin, a second portion of the filler and said catalyst.

8. A compound according to claim 7, wherein the ratio of the two pastes if 1:1 by weight.

9. A compound according to claim 7, wherein the ratio of the first paste to the second paste is 9:1 by weight.

10. A compound according to claim 7, wherein the organopolysiloxane is a silicone oil.

11. A condensation cross-linking molding or lining compound based on silicones consisting essentially of
    (a) an organo polysiloxane comprising two or more reactive hydroxyl reactive end groups, (b) a catalyst comprising a liquid or pasty curing component comprising a metal salt of a monocarboxylic acid ester, (c) a silicic acid ester cross-linking agent, (d) a filler and (e) an isoparaffin having 8 to 24 carbon atoms.

12. A compound according to claim 11, wherein said isoparaffin is selected from the group consisting of isohexadecane, isoeicosane and mixtures thereof.

13. A compound according to claim 11, wherein the isoparaffin is contained in an amount of 1 to 50% by weight.

14. A compound according to claim 11, wherein the isoparaffin is contained in an amount of 5 to 30% by weight.

15. A compound according to claim 11, wherein the filler is selected from the group consisting of powdered quartz, crystobalite, calcium sulphate, diatomaceous earth, talcum, calicum carbonate and precipitated and pyrogenically prepared silicone dioxide.

* * * * *